(12) United States Patent
Thoes et al.

(10) Patent No.: US 7,975,842 B2
(45) Date of Patent: Jul. 12, 2011

(54) OUTER PACKAGING SYSTEM FOR MEDICAL CONSUMABLES

(75) Inventors: Bruno Thoes, Quierschied (DE); Udo Manser, Schwetzingen (DE); Helmut Leininger, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 992 days.

(21) Appl. No.: 11/612,889

(22) Filed: Dec. 19, 2006

(65) Prior Publication Data
US 2007/0151884 A1    Jul. 5, 2007

(30) Foreign Application Priority Data
Dec. 23, 2005   (EP) .................................. 05 028 293

(51) Int. Cl.
*B65D 81/26*   (2006.01)
*G01N 21/00*   (2006.01)

(52) U.S. Cl. ........................................ 206/204; 422/66

(58) Field of Classification Search .............. 206/569, 206/570, 438, 440, 204; 221/69–133; 220/520, 220/578, 579, 200, 502; 422/66, 67, 56, 422/58, 61, 68.1
See application file for complete search history.

(56) References Cited

U.S. PATENT DOCUMENTS

| | | | | |
|---|---|---|---|---|
| 2,533,806 A | * | 12/1950 | Holzapfel | 206/221 |
| 2,583,001 A | * | 1/1952 | Magers | 47/41.1 |
| 3,918,578 A | * | 11/1975 | Cullen et al. | 206/204 |
| 4,146,277 A | * | 3/1979 | Santoro | 96/117.5 |
| 4,834,234 A | | 5/1989 | Sacherer et al. | |
| 5,279,025 A | * | 1/1994 | Kinast | 29/436 |
| 5,947,274 A | * | 9/1999 | Taskis et al. | 206/204 |
| 6,050,400 A | * | 4/2000 | Taskis et al. | 206/204 |
| 2005/0118071 A1 | | 6/2005 | Sacherer et al. | |

FOREIGN PATENT DOCUMENTS

| | | |
|---|---|---|
| DE | 35 19 296 A1 | 1/1986 |
| DE | 37 15 938 A1 | 11/1988 |
| DE | 198 19 407 A1 | 11/1999 |
| DE | 103 53 445 A1 | 6/2005 |
| EP | 1 500 925 | 1/2005 |
| WO | WO 02077522 A2 * | 10/2002 |

* cited by examiner

*Primary Examiner* — J. Gregory Pickett
*Assistant Examiner* — Ernesto A Grano
(74) *Attorney, Agent, or Firm* — Bose McKinney & Evans LLP

(57) ABSTRACT

The invention relates to a packaging system for medical consumables, in particular test elements. The packaging system comprises an outer packaging, which accommodates a first desiccant supply, and a magazine with an unused test element supply. In the closed state of the outer packaging, the first desiccant supply of the outer packaging acts on the interior of the magazine via a connection that permits water vapor diffusion. In exemplary embodiments, the magazine includes a second desiccant supply. The communication of water vapor between the magazine and outer package reduces the load on the desiccant supply in the magazine.

37 Claims, 3 Drawing Sheets

PRIOR ART

PRIOR ART

OUTER PACKAGING SYSTEM FOR MEDICAL CONSUMABLES

RELATED APPLICATIONS

This application claims priority to EP 05028293.8, filed Dec. 23, 2005.

BACKGROUND

The present invention relates to a packaging system for medical consumables, in particular test elements which are accommodated in a magazine that can be removed from an outer packaging.

DE 19819407A1 relates to a test strip container for measurement appliances that work with disposable test strips. These disposable test strips are generally delivered to a sensor for measurement purposes. The container in which the disposable strips are accommodated comprises two parts, the test strips being stored in the first part, and the used test strips being collected in the second part.

Medical consumables accommodated in a magazine, for example test elements used in measurement appliances for blood sugar measurement, for lactate measurement or for cholesterol determination, are packed in an outer packaging in order to protect the medical consumables from environmental influences. Test elements for medical purposes are particularly sensitive to environmental fluctuations and in particular to moisture. For this reason, magazines in which a number of test elements are stored are placed into a sealed outer package in order to avoid entry of moisture into the outer package and, consequently, to avoid the magazine and test elements accommodated in the outer package becoming damaged by penetration of moisture.

The outer package, which is substantially impervious to water vapor and is accommodated in a sales pack for sales purposes, contains a desiccant supply. The magazine in which the test elements are accommodated also contains a desiccant supply. The desiccant supply located in the magazine with the test elements ensures that the test elements contained in the magazine are protected against exposure to water vapor in the time interval between production of the test elements and their end use. In this way it is possible to ensure that the stability of the test elements is independent of the storage period since, during this interval, the desiccant supply inside the magazine accommodating the test elements takes up diffusing water vapor and keeps it away from the test elements contained in the magazine.

If the magazine is in the form of a cartridge, for example, and contains reels for individual test elements received on a transport band, a quantity of desiccant is generally introduced into the part containing the unused test elements that are typically supplied in the form of a wound-up reel. After being fitted with the transport band on which the individual test elements are received, the cartridge is sealed and inserted into an outer package, for example, in the form of an aluminium pouch, together with a desiccant. The outer package is then sealed. With the outer packaging closed, the supply of desiccant accommodated therein ensures that moisture from the environment does not enter and act on the cartridge during storage.

A disadvantage of the above described arrangement is the fact that, in the manufacturing process, the desiccant and also the test elements are unavoidably charged with water vapor. After the magazine has been prepared, that is to say, after the magazine has been loaded with a number of test elements, the test elements and the desiccant contained in the magazine have been already partially charged with moisture arising from the production process. This means that the supply of desiccant contained in the magazine has only a residual capacity for absorbing moisture. The desiccant supply contained in the magazine first dries the interior of the magazine, while the remaining residual absorption capacity ensures the stability of the test elements in the magazine.

SUMMARY OF THE INVENTION

The present invention provides a packaging system for medical consumables, for example test elements, that prolongs the stability of the packaged test elements.

In one embodiment, while the magazine or inner package accommodating the test elements is stored in the outer packaging, a connection for communicating water vapor is created between the desiccant supply in the outer packaging and the desiccant supply in the magazine accommodating the test elements, and, as long as the outer packaging is closed, this produces a connection between the desiccant accommodated in the outer packaging and the desiccant contained in the magazine. The connection between the desiccant supply in the outer packaging and the desiccant supply contained in the magazine can be created by a spacer, for example, which at one end is connected to the outer packaging, and which at the other end lies between a seal and the housing of the test element magazine accommodated in the outer packaging.

By means of the spacer, which can be designed for example as a band with a porous portion, as a woven structure, as a nonwoven structure, or as a filament structure, an opening is created between the seal of the magazine and the interior of the outer packaging, and this opening exists as long as the magazine having the test elements is located in the substantially water-vapor-impervious shell of the outer package.

As long as the magazine remains in the outer packaging, the desiccant supply accommodated in the outer packaging can absorb moisture from the magazine by way of the opening that is widened by the spacer. The amount of desiccant in the outer packaging is generally much greater than the amount of desiccant in the magazine containing the test elements. In particular embodiments, the desiccant supply accommodated in the outer packaging can be used, on the one hand, to reduce the amount of moisture with which the test elements contained in the magazine are charged as a result of the production process and, on the other hand, to absorb moisture that diffuses into the outer packaging during the storage period.

In one embodiment, as soon as the outer packaging is opened, the opening previously created by the spacer between the magazine housing and the seal and the desiccant supply contained in the outer packaging is closed to what for production reasons is a residual size. In this embodiment, when the outer packaging is opened, the spacer connected to the outer packaging is withdrawn from the opening between the seal and the magazine, as a result of which the opening assumes its residual size. If the spacer is made of a porous material that permits water vapor diffusion, the desiccant supply contained in the outer packaging is able to draw water vapor from the interior of the magazine, and this water vapor can be absorbed by the desiccant supply in the outer package. In another embodiment of the invention, the spacer can be manually withdrawn from the opening between the seal and the magazine after the outer packaging has been opened, so that the seal is substantially closed. According to this variant, the user manually transfers the seal from its inactive or open state occurring in the closed position of the outer package to its closed or active (default) position after the outer package is opened.

After the magazine has been removed from the outer package, the desiccant supply contained in the interior of the magazine ensures the stability of the test elements contained in the magazine, despite residual moisture leakage and environmental fluctuations.

From the time the magazine is removed from the outer package, the desiccant supply contained in the magazine has a smaller water vapor load associated with the production process. One consequence of this is that either the amount of desiccant in the magazine can be decreased, while the other conditions remain identical, thus resulting in a smaller overall size of the magazine containing the test elements, or, while the amount of desiccant introduced into the magazine remains identical, the stability of the test elements contained therein can be considerably increased.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

Corresponding reference numerals are used to indicate corresponding parts throughout the several Figures.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

In the explanations given below, a magazine is to be understood as a receiving element in which a number of test elements are accommodated. The magazine can have a cartridge-type design, in which case the supply of test elements is provided, for example, in the form of reels, with one reel for unused test elements and one reel for used test elements. The magazine can also have a stacked design, in which case individual test elements, for example in the form of strips, can be accommodated in a vertical position, in a horizontal position or in an arrangement in which they are inclined relative to one another. The magazine can also be designed as a disc-shaped body, with individual test elements being received in slits on its circumference, in which case a drive mechanism advances the disc-shaped magazine from test element to test element.

In the explanations given below, test elements are understood as medical consumables which are stored in the magazine, for example, in the form of strips, and are used for evaluating an analyte in a human body fluid, for example blood sugar, lactate, cholesterol and the like. In the explanations given below, an opening is understood as an opening through which the medical consumables, for example in test strip form, are dispensed from the magazine, and which opening can be designed, for example, as a seal applied to the housing of the magazine or as a longitudinal slit with sealing lips, in order to avoid undesired entry of moisture into the interior of the magazine accommodating the test elements.

In the explanations given below, a desiccant supply is understood as a desiccant substrate which is used to take up (absorb) water vapor. The desiccant can be present in powder form and in pouches that are introduced into the interior of the magazine or into the interior of the outer packaging. The desiccant can also be designed as a desiccant body that forms an integral part of the magazine accommodating the test elements.

Figure 1:
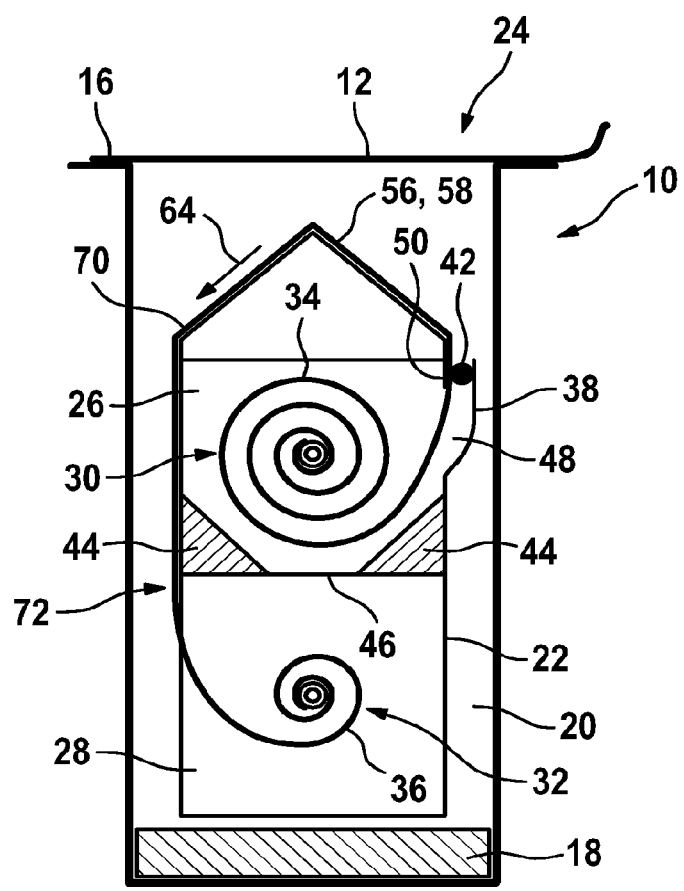
FIG. 1 is a side-sectional view of an outer packaging system according to the prior art in the closed state, with a test element magazine accommodated in the outer package.

FIG. 1 shows an outer package or packaging, known from the prior art, for accommodating a magazine with test elements.

Outer package or packaging 10 for accommodating a magazine 22 is generally made of a material that is substantially impervious to water vapor. The outer packaging 10 according to the depiction in FIG. 1 comprises a schematically indicated closure piece 12 which is connected on one side 16 to the outer packaging 10. To remove the magazine 22 accommodated in the water-vapor-impervious outer packaging 10, the closure piece 12, shown in the closed state 24, is detached at one side. The outer packaging 10 comprises a first desiccant supply 18 which, in the view according to FIG. 1, lies on the bottom of the outer packaging 10. The first desiccant supply 18 can be provided in powder form, and the powder can be accommodated in a bag. In addition, it is also possible to design the first desiccant supply 18 as a desiccant body that is integrated into the underside of the outer packaging 10.

The magazine 22 is located in a hollow space 20 of the outer packaging 10. The magazine 22 includes a first magazine part 26 and a second magazine part 28. An unused test element supply 30 is accommodated in the first magazine part 26, while a used test element supply 32 is accommodated in the second magazine part 28. Thus, if the magazine 22 has a cartridge-type design, the unused test element supply 30 can be accommodated in the form of a fresh reel 34 in the first magazine part 26, whereas, in the second magazine part 28, the used test element supply 32 is accommodated in the form of a used reel 36. An opening of the magazine 22 is indicated by reference number 48. The opening is closed by means of a spring element 38 and by means of a seal 42 connected to the spring element 38. In the view according to FIG. 1, the seal 42 is applied against a magazine-side abutment 50 of the magazine 22. In the view according to FIG. 1, the individual test elements stored on the fresh reel 34 of the unused test element supply 30 are guided by means of a transport band 56 around the outer face of the housing of the magazine 22 and, in doing so, they pass the opening 48. After the test element has been used by the user, i.e., after the test element has been wetted with a human body fluid for determination of an analyte contained in the latter, the used test element is wound up on the used reel 36 in the second magazine part 38 of the magazine 22.

A second desiccant supply 44 is accommodated in the first magazine part 26 of the magazine 22. The first magazine part 26 and the second magazine part 28 are separated from one another by a dividing wall 46. The second desiccant supply 44 stored in the first magazine part 26 is used for desiccating the unused test element supply 30.

Figure 2:
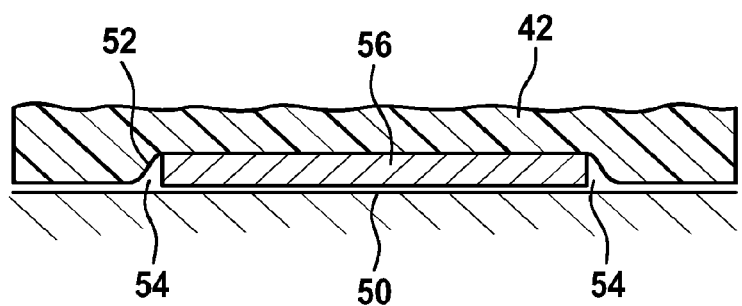
FIG. 2 is a cross-sectional view of the magazine opening for the transport band guided between magazine housing and seal.

In the view according to FIG. 2, the opening of the magazine is depicted on an enlarged scale.

In the state shown in FIG. 2, the seal 42, acted upon by the spring element 38, is applied against the magazine-side abutment 50. By virtue of the elastic properties of the sealing element 42, a contact face 52 of the seal 42 bears on a transport band 56, as shown in FIG. 2. In this way, the opening 48 of the magazine 22 is reduced to a minimum size permitting a residual leakage. The residual leakage that can take place through the opening 48 in the active state 42 is permitted by gaps 54 which arise alongside a transport band 46 (to name one example of a test element carrier) because of the limited deformability of the seal 42. The gaps 54 occur in different geometries depending on the contact pressure generated by the spring element 38 and depending on the age of the elastic sealing material of the seal 42. The transport band 56 transporting the test elements is pressed against the magazine-side abutment 50 by means of the seal 42 that is acted on by the leaf spring 38.

Figure 3:
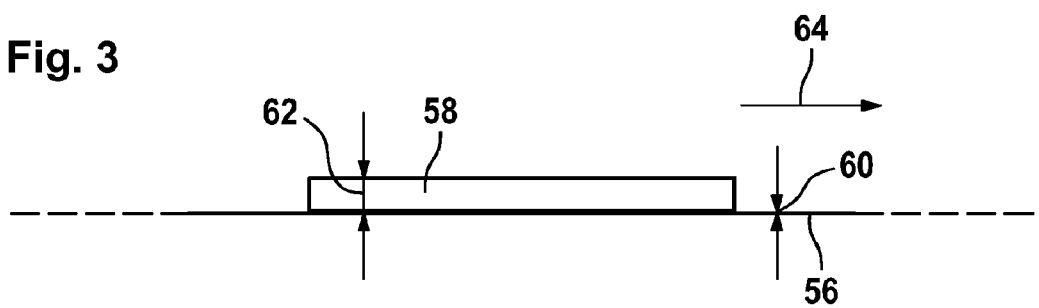
FIG. 3 is a schematic view of the transport band, with an individual test element shown in a side view but not true to scale.

FIG. 3 is a schematic side view of the transport band depicted in FIG. 2.

From the view according to FIG. 3, it emerges that, in the case of a transport band 56 acting as carrier for an individual test element 58, there is a first thickness 60, namely, the thickness of the transport band 56, and the combination of test element 58 and transport band 56 gives a second thickness 62. It is evident from this that the opening 48 between the seal 42 and the magazine-side abutment 50 of the magazine 22 is opened alternately to the first thickness 60 and, during passage of a test element 58, to the second thickness 62.

Because of the seal 42 bearing against the magazine-side abutment 50, the embodiment of an outer packaging system shown in FIGS. 1 to 3 does not contribute to drying the unused test element supply 30 accommodated in the interior of the magazine 22, because the opening 48, as is shown in FIG. 2, is reduced to a minimum. In this case, only the second desiccant supply 44 is active in drying the unused test element supply 30 in the first magazine part 26.

Figure 4:
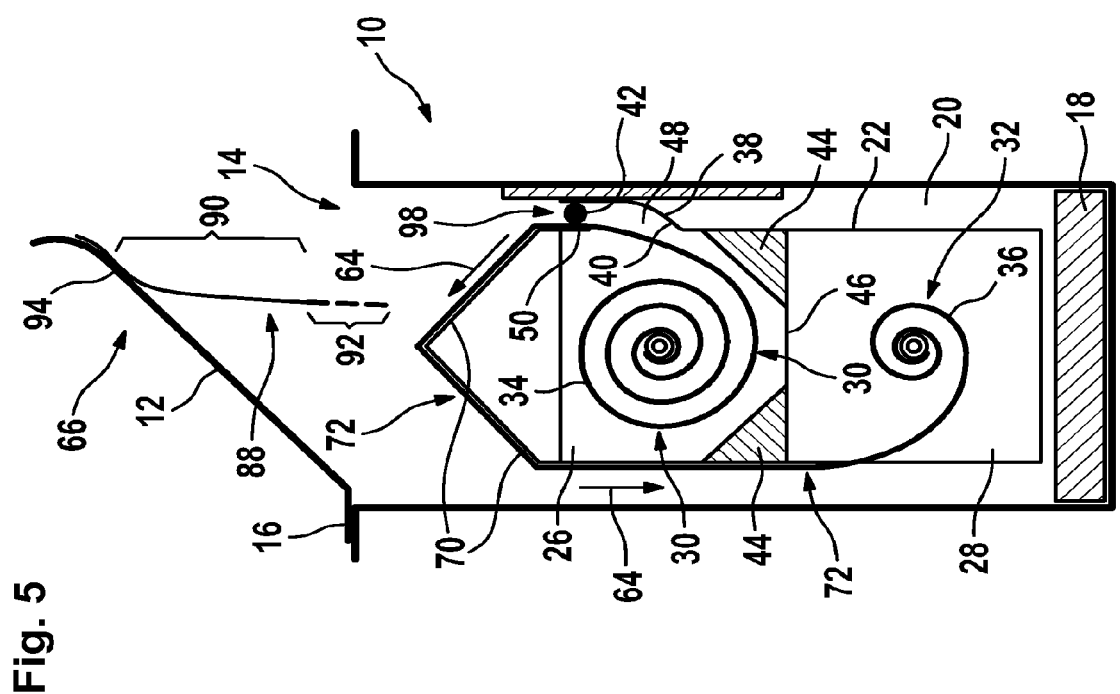
FIG. 4 is a side-sectional view showing the spacer connected to the outer packaging, for deactivating a seal on the housing of the magazine when the outer packaging is closed in accordance with the present teachings.

FIG. 4 shows the outer packaging system in accordance with exemplary embodiments of the present disclosure in the closed state.

The outer packaging system comprises the outer package or packaging 10, while the closure piece 12 is located in the closed position 24. The closure piece 12 is connected at the hinge 16 to the water-vapor-impervious outer packaging 10. The first desiccant supply 18 and the inner package or magazine 22 are both accommodated in the hollow space 20 of the outer packaging 10. The magazine 22 is divided by the dividing wall 46 into the first magazine part 26 and the second magazine part 28. The unused test element supply 30 in the form of the fresh reel 34 is accommodated in the first magazine part 26, whereas the used test element supply 32 in the form of a used reel 36 is located in the second magazine part 28. In the view according to FIG. 4, the test elements 58 are formed on a transport band 56 which is wound up on the fresh reel 34 and which leaves the first magazine part 26 by way of the opening 28, so as to be conveyed in the advance direction 64 around the outer face 70 of the magazine 22 and into the second magazine part 28, in which the used test element supply 32 in the form of the used reel 36 is located.

From the view according to FIG. 4, it will be seen that a spacer 88 is located on the underside of the closure piece 12, at a connection point 94. At the connection point 94, it is connected to the underside of the closure piece 12. The end of the spacer 88 directed away from the connection point 94 extends into the opening 48 of the magazine 22. The spacer 88 can comprise a first portion 90, and also a second portion 92, which is preferably made from a porous material that permits water vapor diffusion. The second portion 92 of the spacer 88 can be designed in the form of a porous band, a nonwoven, a filament structure or the like. A ramp-shaped elevation, a wedge, a cylinder, a block or the like can also be formed on the second portion 92 of the spacer 88, and the second portion 92 of the spacer 88 can also be designed in the form of a band with an aperture, for example a hole, an oblong hole or a number of slits. The spacer 88 or its second portion 92 is preferably made of a chemically inactive material. This material can permit water vapor diffusion by virtue of its material properties. On the other hand, water vapor diffusion from the interior of the magazine 22 into the closed outer packaging 10 can be permitted by the aforementioned list of variants in terms of the geometry of the spacer 88 or of its second portion 92 in the form of a band with an opening, whether holes, oblong holes, slits or the like, or by provision with a wedge, a ramp, a cylinder or the like.

By virtue of the second portion 92 of the spacer 88 extending into the opening 48 of the magazine 22, the seal 42 assumes a deactivated state 96 in which a sealable passageway or opening extends from the magazine to the interior of the outer packaging. This means that the opening 48 in the area of the seal 42 and of the outer face 70 of the magazine 22 remains opened by virtue of the spacer 88 that has been inserted into it. In the deactivated state 96 of the seal 42, the second desiccant supply 44 accommodated in the first magazine part 26 accordingly communicates with the first desiccant supply 18 located in the hollow space 20 of the water-vapor-impervious outer packaging 10. This has the effect that the unused test element supply 30 stored in the first magazine part 26 can be desiccated not only by the second desiccant supply 44 inside the magazine 22, but also by the first desiccant supply 18 provided in the outer packaging 10. As long as the closure piece 12 of the outer packaging 10 remains in the closed position 24, an end of the spacer 88 protrudes into the opening 48 and enlarges the latter in such a way that the first desiccant supply 18 in the hollow space 20 of the outer packaging 10 participates in desiccating the unused test element supply 30 of the magazine 22. It is thus possible to ensure that, in the closed state of the outer packaging system according to FIG. 4, the second desiccant supply 44 inside the first magazine part 26 of the magazine 22 has a lower production-related moisture load then when the outer packaging 10 is opened and the first desiccant supply 18 is thus no longer active. In this way, the amount of the second desiccant supply 44 stored in the first magazine part 26 can be reduced, while other conditions remain identical, so that the magazine 22 as a whole can be made smaller, or, while keeping an identical amount of the second desiccant supply 44, the stability of the unused test element supply 30 can be prolonged, since the preloading of the second desiccant supply 44 has become smaller.

Figure 5:
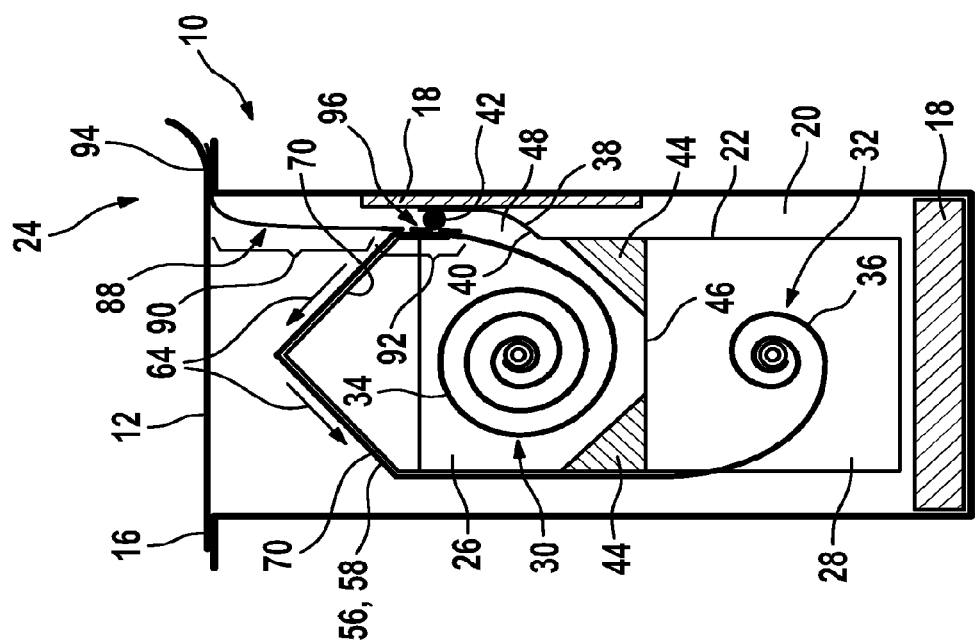
FIG. 5 is a side-sectional view showing the opened outer packaging with the spacer removed from the opening in accordance with the present teachings.

The view according to FIG. 5 shows the outer packaging system according to FIG. 4 in the opened state.

In FIG. 5, the closure piece 12 of the substantially water-vapor-impervious outer packaging 10 is opened, as indicated by reference number 66. During the opening process, the spacer 88, connected to the closure piece 12 at the connection point 94, is withdrawn from the sealable opening 48, in particular from the area between the seal 42 and the magazine-side abutment 50. The seal 42 now assumes its activated or sealed state 98 and seals off the first part 26 of the magazine 22 in which the unused test element supply 30 is contained. The spacer 88 assumes its position shown in FIG. 5. Since the second portion 92 of the spacer 88 is no longer located between the seal 42 and the magazine-side abutment 50, the sealable opening 48 between the seal 42 and the magazine-side abutment 50 recovers its original size, as a result of the pretensioning force of the spring element 38, which can be designed as a leaf spring 40. In another embodiment, the spacer 88 may not be connected to the closure piece 12. In this case, the user can manually withdraw the spacer 88 from the opening 48 of the magazine 22 after opening the outer packaging 10. By means of this manual intervention on the part of the user, the seal 42 is also transferred from its deactivated (open) state 96 to its activated (closed) state 48. After withdrawal of the magazine 22 from the opened outer packaging 10, the seal 42 ensures that the supply of test elements 48 contained in the magazine 22 is substantially sealed off from the environment. With the water-vapor-impervious outer packaging 10 in the opened state, the magazine 22, with the unused test element supply 30 accommodated therein, is removed from the outer packaging 10. After the water-vapor-impervious outer packaging 10 has been opened, the unused test element supply 30 is now desiccated by means of the second desiccant supply 44, which is accommodated in the first magazine part 26 and which can be present therein in the form of a desiccant body 82 or also as a powder enclosed in a bag.

Since the unused test element supply 30 is desiccated by the first desiccant supply 18 and the second desiccant supply 44 in the closed state 24, with the seal 42 in the inactive state 96, i.e., sealed or closed, the second desiccant supply 44 has a smaller preload after the outer packaging 10 is opened as in FIG. 5, as a result of which the on-board stability of the unused test element supply 30 accommodated in the first magazine part 26 of the magazine 22 can be increased. By virtue of the lower preloading of the second desiccant supply 44 in the magazine 22, the amount of the second desiccant supply 44 to be introduced into the magazine 22 can on the one hand be reduced, as a result of which the latter can be made smaller. On the other hand, as the embodiments that the two desiccant supplies 18 and 44 communicate with one another in the closed state 24 of the outer packaging system, it is possible to increase the stability of the unused test element supply 30 after the closure piece 12 of the water-vapor-impervious outer packaging 10 is opened. This in turn is user-friendly and also permits an increase in the number of test elements 58 to be stored in the magazine 22, whether they be in reel form, as explained above, or in the form of stacked test elements 58 in a vertical, horizontal or inclined arrangement inside a magazine 22.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which the invention pertains and which fall within the limits of the appended claims.

LIST OF REFERENCE NUMBERS outer packaging
closure piece
withdrawal opening
hinge for closure piece
first desiccant supply
hollow space of outer packaging 10
magazine
closed position of closure piece 12
first magazine part
second magazine part
unused test element supply
used test element supply
fresh reel
used reel
spring element
leaf spring
seal
second desiccant supply
dividing wall
sealable opening
magazine-side abutment
contact face of seal
gap
transport band
test element
thickness of transport band
thickness of transport band+test element
conveying direction
opened position
outer face of magazine
path of transport band
spacer
first portion of spacer
second portion of spacer
connection point of closure piece 12
deactivated state of seal 42
activated state of seal 42

What is claimed is:

1. A packaging system for medical consumables, comprising:
   an outer packaging containing a first desiccant supply and a magazine, the magazine having an unused test element supply, a second desiccant supply and a seal; and
   the outer packaging having a closed state in which the first desiccant supply acts on the interior of the magazine via a connection that permits water vapor diffusion; the outer packaging being connected to the seal when the outer packaging is in the closed state,
   wherein, opening the outer packaging closes the seal.

2. The packaging system of claim 1, wherein when the outer packaging is in the closed state, the seal assumes a deactivated state which permits water vapor diffusion into the outer packaging.

3. The packaging system of claim 2, further comprising a spring element which acts on the seal.

4. The packaging system of claim 2, wherein the seal is positioned in a recess of the magazine or is secured to a spring element.

5. The packaging system of claim 2, further comprising a spacer connected to the outer packaging, wherein, in the closed state of the outer packaging, the spacer holds the seal in its deactivated state.

6. The packaging system of claim 5, wherein the spacer comprises a first portion and a second portion, the second portion configured to permit water vapor diffusion therethrough.

7. The packaging system of claim 6, wherein the second portion comprises a porous band, a nonwoven, a filament structure or a woven fabric.

8. The packaging system of claim 6, wherein the first portion is secured at a connection point to a portion of the outer packaging that is openable.

9. The packaging system of claim 2, wherein, in the deactivated state, the seal maintains open an enlarged cross section of an opening leading to the unused test element supply in the magazine.

10. The packaging system of claim 2, wherein the seal, when closed, contacts a portion of the unused test element supply located in the opening.

11. The packaging system of claim 1, wherein the first and second desiccant supplies comprise desiccant bodies located in the outer packaging and in the magazine, respectively.

12. The packaging system of claim 1, wherein the outer packaging is substantially impervious to water vapor.

13. The packaging system of claim 1, wherein the unused test element supply comprises a magazine that houses a fresh reel having a transport band with test elements housed in the magazine.

14. The packaging system of claim 1, wherein the first desiccant supply is positioned opposite an opening of the magazine.

15. The packaging system of claim 1, wherein the second desiccant supply is contained in a first part of the magazine that is separate from a second part of the magazine.

16. The packaging system of claim 1, wherein the outer packaging is connected to the seal indirectly via a spacer when the outer packaging is in the closed state.

17. A packaging system for medical consumables, comprising:
an inner package containing a medical consumable and a first desiccant;
an outer package containing a second desiccant and the inner package; and
the inner package comprising a seal having an activated state and a deactivated state, wherein, in the activated state communication of water vapor through the seal is substantially prevented, further wherein the deactivated state allows communication of water vapor between the inner and outer packages, wherein in the deactivated state the second desiccant absorbs moisture from the inner package.

18. The packaging system of claim 17, wherein the seal has a removable element positioned therein.

19. The packaging system of claim 18, wherein the removable element comprises a porous band, a nonwoven, a filament structure or a woven fabric.

20. The packaging system of claim 18, wherein the removable element is connected to the outer package, the packaging system being configured to remove the removable element from the sealable opening when the outer package is opened.

21. The packaging system of claim 18, further comprising a spring element which acts on the seal.

22. The packaging system of claim 17, wherein the inner package comprises a magazine and the medical consumable comprises a plurality of test elements.

23. The packaging system of claim 22, wherein the outer package comprises a pouch.

24. The packaging system of claim 17, wherein the outer package is substantially impervious to water vapor.

25. The packaging system of claim 17, wherein the medical consumables comprise a plurality of test elements wound on a reel and the inner package comprises a magazine containing the reel.

26. The packaging system of claim 17, further comprising a spacer connected to the outer package, wherein the spacer holds the seal in the deactivated state.

27. The packaging system of claim 26, wherein the spacer comprises a first portion and a second portion, the second portion configured to permit water vapor diffusion therethrough.

28. The packaging system of claim 27, wherein the second portion comprises a porous band, a nonwoven, a filament structure or a woven fabric.

29. The packaging system of claim 27, wherein the first portion is secured at a connection point to a portion of the outer package that is openable.

30. The packaging system of claim 17, wherein the first and second desiccant supplies comprise desiccant bodies.

31. The packaging system of claim 17, wherein, in the deactivated state, the seal maintains open an enlarged cross section of an opening leading to the medical consumable in the inner package.

32. The packaging system of claim 17, wherein the second desiccant is positioned outside the inner package and inside the outer package.

33. The packaging system of claim 17, wherein the first desiccant supply is contained in a first part of the inner package that is separate from a second part of the inner package.

34. The packaging system of claim 17, wherein the seal is manually transferrable from the deactivated state to the activated state.

35. The packaging system of claim 17, wherein the outer package is connected to the seal when the outer package is closed.

36. The packaging system of claim 17, wherein the outer package has a closed state in which the outer package is substantially impervious to water vapor, wherein, in the closed state of the outer package, the seal is in the deactivated state.

37. The packaging system of claim 36, wherein opening the outer package places the seal in the activated state.

\* \* \* \* \*